United States Patent

Berner et al.

[11] Patent Number: 4,699,949
[45] Date of Patent: Oct. 13, 1987

[54] HARDENING OF ACID-HARDENABLE COMPOSITIONS CONTAINING A BLOCKED HARDENING CATALYST, USING HEAT

[75] Inventors: Godwin Berner, Binningen; Werner Rutsch, Fribourg, both of Switzerland

[73] Assignee: Ciba-Geigy Corporation, Ardsley, N.Y.

[21] Appl. No.: 747,147

[22] Filed: Jun. 20, 1985

Related U.S. Application Data

[63] Continuation-in-part of Ser. No. 623,651, Jun. 22, 1984, abandoned.

[30] Foreign Application Priority Data

Jul. 1, 1983 [CH] Switzerland ......................... 3636/83

[51] Int. Cl.$^4$ ............................................. C08L 61/00
[52] U.S. Cl. ................................. 525/162; 525/132; 525/163; 525/165; 525/176; 525/348; 525/351; 525/353; 525/442; 525/443; 525/480; 525/497; 525/498; 525/509
[58] Field of Search ............... 525/509, 162, 163, 165, 525/176, 348, 351, 353, 442, 443, 480, 497, 498

[56] References Cited

U.S. PATENT DOCUMENTS 3,474,654 10/1969 White .................................. 524/39 X
4,431,774 2/1984 Felder-Schraner ................. 525/162
4,477,618 10/1984 Singer et al. ........................ 524/157
4,510,290 4/1985 Kirchmayr et al. ................ 525/162

FOREIGN PATENT DOCUMENTS 2736231 2/1979 Fed. Rep. of Germany .

Primary Examiner—Theodore E. Pertilla
Attorney, Agent, or Firm—Luther A. R. Hall

[57] ABSTRACT

Compounds of formula I or II

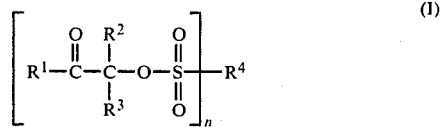

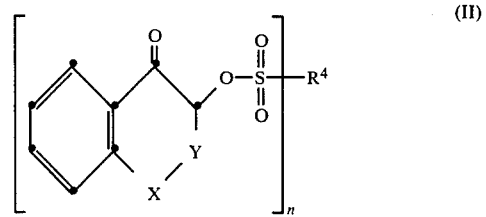

in which n is 1 or 2, $R^1$ is phenyl, substituted phenyl, alkyl, substituted alkyl, hydrogen, —OH or amino, $R^2$ is hydrogen, $R^3$ is hydrogen, alkyl, substituted alkyl, phenyl or substituted phenyl, $R^4$ is alkyl, phenyl, substituted phenyl, alkylene or arylene, X is —O—, —S—, —CH$_2$— and Y is a direct bond or —CH$_2$— are latent hardening catalysts for acid curable resins. The catalysts are activated by heat and are used in heat-hardening high-solids industrial varnishes and for coil-coatings, can and wood varnishes.

14 Claims, No Drawings

HARDENING OF ACID-HARDENABLE COMPOSITIONS CONTAINING A BLOCKED HARDENING CATALYST, USING HEAT

This is a continuation-in-part of application Ser. No. 623,651 filed on June 22, 1984, now abandoned.

The present invention relates to a process in which an acid-hardenable composition containing a latent hardening catalyst is hardened by heat, and to some of these latent hardening catalysts and compositions thereof.

It is known that acid-hardenable resins are chiefly used as binders in varnishes, printing inks and paints. Since most of the acids used as hardening catalysts together with the resin already cause slow hardening at room temperature, they are added to the resin (or the particular corresponding composition) only shortly before its use.

In order to avoid this disadvantage, one-component systems have been proposed, in which a masked hardening catalyst is already present in the acid-hardenable composition. The acid necessary for hardening can be liberated from this catalyst on the one hand by irradiation with short-wavelength light and subsequent warming or on the other hand merely by warming.

Examples of latent hardening catalysts which are activated by the method of "irradiation with short-wavelength light and subsequent warming" are the sulfonic acid esters described in German Offenlegungsschrift No. 1,919,678.

Examples of latent hardening catalysts which are activated by warming are amine salts of aromatic sulfonic acids, such as the pyridine salts proposed in U.S. Pat. No. 3,474,054, but these may have the disadvantages that they already cause slow hardening during storage, that odour problems arise and that problem-free electrostatic spraying is not guaranteed. In addition, sulfonate esters are known as catalysts in acid-hardenable compositions, as described in U.S. Pat. No. 4,281,075. However, these compounds do not fulfill in all respects the requirements placed on them, for example good storage stability and a high rate of release on heat treatment.

It has now been found that α-sulfonyloxycarbonyl compounds which are easy to prepare industrially substantially fulfill these requirements. Furthermore, they lead to hardly any yellowing after the hardening activated by heat. It is surprising that the compounds used as latent hardening catalysts in the process according to the invention already exhibit a high rate of release of the sulfonic acid at relatively low temperatures. Whilst only an unsatisfactory hardening can be achieved below and at 100° C., the catalysts to be used according to the invention are outstandingly suitable at temperatures from 110° C. for heat-hardening of acid-hardenable compositions.

The present invention relates to a process in which an acid-hardenable composition containing at least one latent hardening catalyst of the formula (I) or (II)

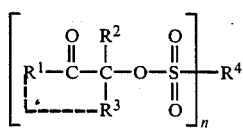

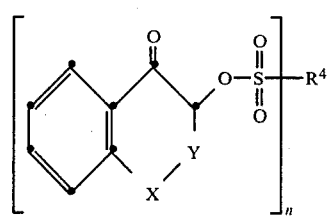

in which, in both formulae, n is 1 or 2, $R^1$ is phenyl which is unsubstituted or mono-, di- or tri-substituted by —Cl, —Br, $C_1$–$C_{12}$-alkyl, $C_1$–$C_4$-alkoxy, phenyl or phenoxy, naphthyl which is unsubstituted or mono-, di- or tri-substituted by —Cl, —Br or $C_1$–$C_{12}$-alkyl, $C_1$–$C_{12}$-alkyl which is unsubstituted or mono- or poly-substituted by —OR, —Cl, —Br, phenyl or cycloalkyl, where R is hydrogen, $C_1$–$C_4$-alkyl or —$SO_2$—$R^4$, where $R^4$ is as defined below, or in which $R^1$ is $C_1$–$C_{12}$-alkenyl which is unsubstituted or substituted by phenyl, or hydrogen, —OH, $C_5$–$C_7$-cycloalkoxy or $C_5$–$C_7$-cycloalkyl, or —$NH_2$, —$NHR^5$, —$N(R^5)_2$ or —N—H—CO—$R^5$, where $R^5$ is $C_1$–$C_4$-alkyl or phenyl, or in which $R^1$ is morpholinyl, piperidinyl, pyridyl, furyl, thienyl, tetrahydrofuranyl, tetrahydronaphthyl or indolyl, $R^2$ is hydrogen, $R^3$ is hydrogen, $C_1$–$C_8$-alkyl which is unsubstituted or mono- or poly-substituted by —OR, —Cl, —CN, —COOH, phenyl, chlorophenyl, $C_7$–$C_{10}$-alkylphenyl or $C_7$–$C_{10}$-alkoxyphenyl, where R is hydrogen, $C_1$–$C_4$-alkyl or —$SO_2$—$R^4$, where $R^4$ is as defined below, or in which $R^3$ is phenyl which is unsubstituted or mono- or poly-substituted by —Cl, —Br, $C_1$–$C_{12}$-alkyl, $C_1$–$C_4$-alkoxy, phenyl or phenoxy, or —CN, —COOH, benzoyl, —$CONH_2$, —$CONHR^5$, $CON(R^5)_2$,

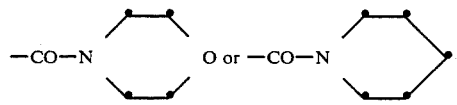

where $R^5$ is $C_1$–$C_4$-alkyl or phenyl, or $R^1$ and $R^3$, together with the carbon atoms to which they are bonded, form a $C_5$–$C_7$-cycloalkyl ring, X is —O—, —S—, —$SO_2$—, —$CH_2$—, —$C(CH_3)_2$— or >N—$COR^5$, where $R^5$ is $C_1$–$C_4$-alkyl or phenyl, Y is a direct bond or —$CH_2$— and, if n=1, $R^4$ is $C_1$–$C_{18}$-alkyl, phenyl which is unsubstituted or mono-, di- or tri-substituted by halogen, $C_1$–$C_{18}$-alkyl, $C_1$–$C_4$-alkoxy, —CONH—, ($C_1$–$C_4$-alkyl), —CONH—$C_6H_5$, —$NO_2$ or benzoyl, naphthyl which is unsubstituted or mono-, di- or tri-substituted by halogen, $C_1$–$C_{12}$-alkyl or $C_1$–$C_4$-alkoxy, and $R^4$ is moreover $C_5$–$C_6$-cycloalkyl, $C_7$–$C_9$-aralkyl, camphoryl, —$CF_3$, —$CCl_3$ or —$NH_2$, and, if n=2, $R^4$ is a —$(CH_2)_m$—group, where m is a number from 2 to 8, or is phenylene or naphthylene, each of which is unsubstituted or mono- or poly-substituted by $C_1$–$C_{12}$-alkyl, is hardened by heat at a temperature of 110° C. to 300° C.

A $C_1$–$C_{12}$-alkyl substituent of a phenyl or naphthyl radical $R^1$ is a straight-chain or branched substituent, for example methyl, ethyl, n-propyl, isopropyl, n-butyl, isobutyl, sec.-butyl, tert.-butyl, straight-chain or branched pentyl, hexyl, heptyl, octyl, nonyl, decyl, undecyl or dodecyl, but especially a $C_1$–$C_4$-alkyl chain. A $C_1$–$C_4$-alkoxy substituent of a phenyl radical $R^1$ is, for example, methoxy, ethoxy, propoxy or tert.-butoxy. A $C_1$–$C_2$-alkyl radical $R^1$ is a straight-chain or branched alkyl group, such as methyl, ethyl, propyl, isopropyl, butyl, tert.-butyl, pentyl, hexyl, heptyl, octyl, nonyl, decyl, 2-ethylhexyl, undecyl or dodecyl, preferably a $C_1$–$C_4$-alkyl chain.

All the mono-hydroxy position isomers are possible for a $C_1$–$C_{12}$-alkyl radical $R^1$ which is substituted by —OH, but one OH group on the $C_1$ or $C_2$ atom on the particular alkyl chain is preferred, for example hydroxymethyl, 1-hydroxyethyl, 2-hydroxyethyl, 1-hydroxy-n-propyl, 2-hydroxy-n-propyl, 1-hydroxy-isopropyl, 2-hydroxy-isopropyl or 1-hydroxydodecyl. A $C_1$–$C_{12}$-alkyl radical $R^1$ which is substituted by —Cl or —Br can preferably contain 1 to 4 of these halogen atoms, but, in particular, the $C_1$ to $C_4$ atoms of the particular alkyl chain are substituted, for example monochloromethyl, monobromomethyl, dichloromethyl, trichloromethyl, 1,2-dichloroethyl, 1,2,3-trichloropropyl, and 1,2,3,4-tetrachlorobutyl. A cycloalkyl radical as a substituent of a $C_1$–$C_{12}$-alkyl radical $R^1$ is cyclopentyl or cyclohexyl, the particular alkyl chains being substituted only once on their $C_1$ to $C_6$ atoms, such as cyclopentylmethyl, 1-cyclopentylethyl, 2-cyclopentylethyl, cyclohexylmethyl, 1-cyclohexylethyl and 2-cyclohexylethyl. A $C_1$–$C_{12}$-alkyl radical $R^1$ which is substituted by phenyl can be substituted on the alkyl chain by a phenyl group in any position, but preferably on the $C_1$ atom of the particular alkyl chain, for example benzyl, α-methylbenzyl, 1-phenyl-n-propyl, 1-phenyl-n-butyl or α,α-dimethylbenzyl.

A $C_1$–$C_{12}$-alkenyl radical as a substituent of $R^1$ preferably has a double bond in the 1,2- or 3,4-position, for example ethenyl, n-prop-1-enyl, iso-prop-1-enyl, n-but-1-enyl, n-but-3-enyl, sec.-but-1-enyl, iso-but-1-enyl, pent-1-enyl, hex-1-enyl, hept-1-enyl, oct-1-enyl, non-5-enyl, dec-1-enyl, undec-3-enyl or dodec-1-enyl.

A $C_1$–$C_{12}$-alkenyl radical $R^1$ which is substituted by phenyl is a straight-chain or branched alkenyl chain which preferably has a double bond in the 1,2- or 3,4-position and a phenyl group on the $C_2$ atom of the particular alkenyl chains, for example 2-phenyl-ethenyl, 2-phenyl-prop-1-enyl and 2-phenyl-but-1-enyl.

A $C_5$–$C_7$-cycloalkoxy radical $R^1$ is for example cyclopentoxy, cyclohexoxy or cycloheptoxy, preferably cyclohexoxy.

A $C_5$–$C_7$-cycloalkyl radical $R^1$ is, for example, cyclopentyl, cyclohexyl or cycloheptyl, preferably cyclohexyl.

$R^5$ is, for example, methyl, ethyl, n-propyl, n-butyl, isopropyl, tert.-butyl or phenyl.

All the position isomers are possible for a thienyl, pyridyl, furyl, indolyl, tetrahydrofuranyl or tetrahydronaphthyl radical $R^1$. However, preferred position isomers are 2-thienyl, 3-pyridyl, 2-furyl, 3-indolyl and 1,2,3,4-tetrahydro-6-naphthyl.

$R^1$ is preferably unsubstituted or substituted phenyl or naphthyl, hydroxyl, or hydrogen.

A $C_1$–$C_8$-alkyl radical $R^3$ is a straight-chain or branched alkyl group, but preferably a straight-chain or branched $C_4$–$C_8$-alkyl group, such as n-butyl, sec.-butyl, tert.-butyl, pentyl, hexyl, heptyl or octyl.

A $C_1$–$C_4$-alkoxy substituent on a $C_1$–$C_8$-alkyl or phenyl radical in $R^3$ or a phenyl or naphthyl radical in $R^4$ is, for example, a methoxy, ethoxy, propoxy or tert.-butoxy substituent.

A $C_7$–$C_{10}$-alkylphenyl or $C_7$–$C_{10}$-alkoxyphenyl substituent on a $C_1$–$C_8$-alkyl radical $R^3$ is, for example, a methyl-, methoxy-, ethyl-, ethoxy-, tert.-butyl or tert.-butoxyphenyl substituent.

A $C_1$–$C_4$-alkyl substituent on a phenyl radical $R^3$ is, for example, methyl, ethyl, n-propyl, iso-propyl, n-butyl or tert.-butyl.

A —CO—NHR$^5$ radical $R^3$, where $R^5$ is $C_1$–$C_4$-alkyl, or a —CO—NH—($C_1$–$C_4$-alkyl) substituent on a phenyl radical $R^4$ is, for example, methyl-, ethyl-, propyl- or n-butyl-NHCO—.

The substituents on a poly-substituted $C_1$–$C_{12}$-alkyl radical in $R^1$ or $C_1$–$C_8$-alkyl radical in $R^3$ can be identical or different and bonded to the same or to different carbon atoms. 1 to 3 identical or different substituents which are on $C_1$ to $C_3$ or on the terminal carbon atom in the particular alkyl chain are preferred.

A cycloalkyl ring formed by $R^1$ and $R^3$, together with the carbon atoms to which they are bonded, is, for example, a cyclopentane, cyclohexane or cycloheptane ring, but in particular a cyclohexane ring.

If n=1, a $C_1$–$C_{18}$-alkyl radical $R^4$ is a straight-chain or branched group, for example methyl, ethyl, propyl, isopropyl, butyl, tert.-butyl, pentyl, hexyl, heptyl, octyl, nonyl, decyl, 2-ethylhexyl, undecyl, dodecyl, tert.-dodecyl, tridecyl, tetradecyl, hexadecyl or octadecyl.

A $C_1$–$C_{18}$-alkyl substituent on a phenyl or naphthyl radical $R^4$ is a straight-chain or branched alkyl group, for example methyl, ethyl, n-propyl, iso-propyl, n-butyl, sec.-butyl, tert.-butyl, pentyl, hexyl, heptyl, octyl, 2-ethylhexyl, nonyl, decyl, undecyl, dodecyl, 1-pentylheptyl, tridecyl, tetradecyl, pentadecyl, hexadecyl, heptadecyl or octadecyl or isomer mixtures thereof, but in particular isomer mixtures with $C_9$–$C_{15}$-alkyl radicals. Alkyl substituents on a tri-alkyl-substituted phenyl radical are lower alkyl substituents, preferably methyl.

Thus, a phenyl radical $R^4$ which is substituted by $C_9$–$C_{15}$-alkyl contains in particular straight-chain alkyl radicals and the phenyl can have linkage points, for example on the nonyl and decyl in the 2-, 3-, 4- or 5-position, the undecyl and dodecyl in the 2-, 3-, 4-, 5- or 6-position and on the tridecyl and tetradecyl in the 2-, 3-, 4-, 5-, 6- or 7-position; mixtures of such phenyl radicals substituted by $C_9$–$C_{15}$-alkyl may also occur here.

A $C_5$–$C_6$-cycloalkyl radical $R^4$ is cyclopentyl or cyclohexyl.

A $C_7$–$C_9$-aralkyl radical $R^4$ is, for example, 1-phenylethyl, 2-phenylethyl or benzyl.

A camphoryl radical $R^4$ is, for example, 10-camphoryl.

If n=2, a —(CH$_2$)m-group $R^4$ is, for example, ethylene, trimethylene, tetramethylene, pentamethylene, hexamethylene or octamethylene.

A $C_1$–$C_{12}$-alkyl substituent on phenylene or naphthylene is a straight-chain or branched alkyl group, for example methyl, ethyl, n-propyl, isopropyl, n-butyl, sec.-butyl, tert.-butyl, pentyl, hexyl, heptyl, octyl, 2-ethylhexyl, nonyl, decyl, 1-butylhexyl, undecyl, dodecyl, 1-pentylheptyl.

If the various phenyl groups in the radicals $R^1$, $R^3$ and $R^4$ are substituted by radicals other than hydrogen atoms, this substitution is in the ortho-, meta- or parapositon, but in particular in the para-position.

If stereoisomeric forms are possible, these are all the isomers, but preferably the naturally occurring isomers.

Examples of individual compounds of the formulae (I) and (II) are:

(a) Formula I, where n=1: 2-[(4-tolylsulfonyl)oxy]-1,2-diphenyl-1-ethanone, 2-[(4-dodecylphenylsulfonyl)oxy]-1,2-diphenyl-1-ethanone, 2-[(phenylsulfonyl)oxy]-1,2-diphenyl-1-ethanone, 2-[(mesitylsulfonyl)oxy]-1,2-diphenyl-1-ethanone, 2-[(4-chlorophenylsulfonyl)oxy]-1,2-diphenyl-1-ethanone, 2-[(4-methoxyphenylsulfonyl)oxy]-1,2-diphenyl-1-ethanone, 2-[(4-acetamidophenylsulfonyl)oxy]-1,2-diphenyl-1-ethanone, 2[(2-nitrophenylsulfonyl)oxy]-1,2-diphenyl-1-ethanone, 2-[(methylsulfonyl)oxy]-1,2-diphenyl-1-ethanone, 2-[(octylsulfonyl)oxy]-1,2-diphenyl-1-ethanone, 2-[(hexadecylsulfonyl)oxy]-1,2-diphenyl-1-ethanone, 2-[(benzylsulfonyl)oxy]-1,2-diphenyl-1-ethanone, 2-[(cyclohexylsulfonyl)oxy]-1,2-diphenyl-1-ethanone, 2-[(trifluoromethylsulfonyl)oxy]-1,2-diphenyl-1-ethanone, 2-[(2-chloroethylsulfonyl)oxy]-1,2-diphenyl-1-ethanone, 2-[(2-naphthylsulfonyl)oxy]-1,2-diphenyl-1-ethanone, 2-[(10-camphorylsulfonyl)oxy]-1,2-diphenyl-1-ethanone, 2-[(4-dodecylphenylsulfonyl)oxy]-1,2-bis-(4-methoxyphenyl)-1-ethanone, 2-[(4-dodecylphenylsulfonyl)oxy]-1,2-bis-(4-chlorophenyl)-1-ethanone, 2-[(4-tolylsulfonyl)oxy]-1,2-bis-(4-tolyl)-1-ethanone, 2-[(4-tolylsulfonyl)oxy]-1-(2-naphthyl)-1-ethanone, 2-[(4-tolylsulfonyl)oxy]-acetic acid, 2-[(phenylsulfonyl)oxy]-acetic acid, 2-[(4-undecylphenylsulfonyl)oxy]-1-ethanal, 2-1[(4-tolylsulfonyl)oxy]-N-acetyl-acetamide, 1-[(4-dodecylphenylsulfonyl)oxy]-2-propanone, 2-[(4-tolylsulfonyl)oxy]-4-methyl-valeric acid, 2-[(4-tolylsulfonyl)oxy]-propionic acid, 2-[(4-tolylsulfonyl)oxy]-dodecanoic acid, 3-[(4-tolylsulfonyl)oxy]-2-butanone, 2-[(4-tolylsulfonyl)oxy]-3-pentanone, 2-[(4-dodecylphenylsulfonyl)oxy]-2-phenyl-acetic acid, 2-[(2-tolylsulfonyl)oxy]-butanal, 3-[(4-tolylsulfonyl)oxy]-4-methyl-2-pentanone, 1-[(3-tolylsulfonyl)oxy]-4-methyl-2-pentanone, 3-[(4-tolylsulfonyl)oxy]-4-heptanone, 2-[(4-dodecylphenylsulfonyl)oxy]-1-phenyl-1-ethanone, 2-[(4-dodecylphenylsulfonyl)oxy]-1-(4-chlorophenyl)-1-ethanone, 2-[(4-dodecylphenylsulfonyl)oxy]1-(4-tolyl)-1-ethanone, 4-[(4-tolylsulfonyl)oxy]-3-octanone, 2-[(4-tridecylphenylsulfonyl)oxy]-1-(4-biphenylyl)-1-ethanone, 2-[(4-tolylsulfonyl)oxy]-1-(4-methoxyphenyl)-1propanone, 2-[(4-tolylsulfonyl)oxy]-cyclohexanone, 2-[(4-tolylsuofnyl)oxy]-cyclopentanone, 2-[(4-tolylsulfonyl)oxy]-cycloheptanone, 1-[(3-tolylsulfonyl)oxy9 -1,3-diphenyl-2-propanone, 2-[(4-dodecylphenylsulfonyl)oxy]-1-(4-dodecylphenyl)-ethanone, 2-[(4-tolylsulfonyl)oxy]-1-(4-dodecylphenyl)-1-ethanone, 1[4-dodecylphenylsulfonyl)oxy]-3-hydroxy-2-propanone, 2[(4-tolylsulfonyl)oxy]-1,3-diphenyl-1,3-propanedione, 3-[(4-tolylsulfonyl)oxy]-2,4-pentanedione, 2-[((4-(1-pentylnonyl)-phenyl)sulfonyl)oxy]-3-methyl-2-(3-chloro-4-methyl-phenyl)-1-butanone, 2-[((4-(1-pentylheptyl)-phenyl)sulfonyl)oxy]-1-2-diphenyl-1-ethanone, 2-[((2,5-dichlorophenyl)sulfonyl)oxy]-1-(2,4,6-trimethylphenyl)-1-butanone, 1-[((4-methoxyphenyl)sulfonyl)oxy]-5,6-dichloro-6-methyl-2-heptanone, 3-[((4-methoxyphenyl)sulfonyl)-oxy]-5,6-dichloro-6-methyl-2-heptanone, 2-[((3-chloro-4-methylphenyl)sulfonyl)oxy]-3-methoxy-1-(4-chlorophenyl)-3-(4-ethoxyphenyl)-1-propanone, 2[((4-(1-propyl-hexyl)phenyl)sulfonyl)oxy]-1,2-bis(3-chloro-4-methylphenyl)-1-ethanone, 2-[(4-tolylsulfonyl)oxy]-propionic acid, 2-[(4-tolylsulfonyl)oxy]butanal and 2-[(4-tolylsulfonyl)oxy]-propionic acid morpholide;

(b) formula I, where n=2: bis-(1,2-diphenyl-2-oxoethyl) 1,4-butanedisulfonate, bis-(1,2-diphenyl-oxoethyl) 1,3-benzenedisulfonate, bis-(2-oxo-2-phenylethyl) 1,5-naphthalenedisulfonate and bis-(2-oxo-propyl) dioctyl-2,6-naphthalenedisulfonate; and (c) formula II: 2-[(4-tolylsulfonyl)oxy]-3,4-dihydro-1(2H)-naphthalenone, 3-[(4-dodecylphenylsulfonyl)oxy]-2,3-dihydro-4H-1-benzopyrane-4-one, 3-(methylsulfonyloxy)-2,3-dihydro-4H-1-benzothiopyran-4-one, 2-[(10-camphorylsulfonyl)oxy]-3(2H)-benzofuranone and 2-[(4-tolylsulfonyl)oxy]-2,3-dihydro-1H-inden-1-one.

A proferred process is that in which an acid-hardenable composition containing at least one hardening catalyst of the formula I with n=1, in which $R^1$ is phenyl which is unsubstituted or substituted by —Cl, —Br or $C_1$–$C_{12}$-alkyl, naphthyl which is unsubstituted or substituted by —Cl, —Br or $C_1$–$C_{12}$-alkyl, or $C_1$–$C_{12}$-alkyl which is unsubstituted or substituted by —OR, —Cl or phenyl, where R is hydrogen, $C_1$–$C_4$-alkyl, or —SO$_2$—$R^4$, where $R^4$ is as defined below, or in which $R^1$ is hydrogen or —OH, $R^2$ is hydrogen and $R^3$ is hydrogen, $C_1$–$C_8$-alkyl which is unsubstituted or substituted by —OR, —Cl, —COOH or phenyl, where R is hydrogen, $C_1$–$C_4$-alkyl or —SO$_2$—$R^4$, where $R^4$ is as defined below, or in which $R^3$ is phenyl which is unsubstituted or substituted by —Cl, —Br, $C_1$ $_l$-$C_4$-alkoxy or $C_1$ $_l$-$C_{12}$-alkyl, $R^4$ is $C_1$–$C_{18}$-alkyl, camphoryl, phenyl which is unsubstituted or substituted by —Cl, —Br, $C_1$ $_l$-$C_{18}$-alkyl or acetamido, or naphthyl which is unsubstituted or substituted by —Cl, —Br or $C_1$–$C_{18}$-alkyl, is hardened by heat.

A particularly preferred process is one in which an acid-hardenable composition containing at least one hardening catalyst of the formula I with n=1, in which $R^1$ is phenyl which is unsubstituted or substituted by —Cl, —Br or $C_1$–$C_4$-alkyl, $C_1$–$C_{12}$-alkyl which is unsubstituted or substituted by —OR, —Cl or phenyl, where R is hydrogen, $C_1$–$C_4$-alkyl or —SO$_2$—$R^4$, where $R^4$ is as defined below, or in which $R^1$ is —OH, $R^2$ is hydrogen and $R^3$ is hydrogen, $C_1$–$C_8$-alkyl which is unsubstituted or substituted by —OR, —COOH or phenyl, where R is hydrogen, $C_1$–$C_4$-alkyl or —SO$_2$—$R^4$, where $R^4$ is as defined below, or in which $R^3$ is phenyl which is unsubstituted or substituted by —Cl, —Br, $C_1$–$C_4$-alkoxy or $C_1$–$C_{12}$-alkyl, and $R^4$ is $C_1$–$C_{18}$-alkyl, phenyl which is unsubstituted or substituted by $C_1$–$C_{15}$-alkyl or naphthyl which is unsubstituted or substituted by $C_1$–$C_{18}$-alkyl, is hardened by heat.

An especially preferred process is one in which an acid-hardenable composition containing at least one hardening catalyst of the formula I with n=1, in which $R^1$ is phenyl which is unsubstituted or substituted by —Cl or $C_1$–$C_4$-alkyl, $C_1$–$C_8$-alkyl which is unsubstituted or substituted by —OR, where R is hydrogen, $C_1$–$C_4$-alkyl or —SO$_2$—$R^4$, where $R^4$ is as defined below, or in which $R^1$ is —OH, $R^2$ is hydrogen and $R^3$ is hydrogen, $C_1$–$C_8$-alkyl which is unsubstituted or substituted by —OR or —COOH, where R is hydrogen, $C_1$–$C_4$-alkyl or —SO$_2$—$R^4$, where $R^4$ is as defined below, or in which $R^3$ is phenyl which is unsubstituted or substituted by —Cl or $C_1$—$C_{12}$-alkyl, and $R^4$ is $C_1$–$C_{18}$-alkyl, phenyl which is unsubstituted or substituted by $C_1$–$C_{15}$-alkyl or naphthyl which is unsubstituted or substituted by $C_1$–$C_{18}$-alkyl, is hardened by heat.

A very especially preferred process is one in which an acid-hardenable composition containing at least one hardening catalyst of the formula I with n=1, in which $R^1$ is phenyl which is unsubstituted or substituted by —Cl or methyl, or is —OH, $R^2$ is hydrogen and $R^3$ is hydrogen, $C_1$–$C_8$-alkyl which is unsubstituted or substituted by —OR, where R is hydrogen, $C_1$–$C_4$-alkyl or —SO$_2$—$R^4$, where $R^4$ is as defined below, or in which $R^3$ is phenyl which is unsubstituted or substituted by methyl, and $R^4$ is methyl, or phenyl which is unsubstituted or substituted by $C_9$–$C_{15}$-alkyl or methyl, is hardened by heat.

A very particularly preferred process is one in which an acid-hardenable composition containing at least one hardening catalyst of the formula I with n=1, chosen from the group consisting of 2-[(4-tolylsulfonyl)oxy]-1,2-diphenyl-1-ethanone, 2-[(4-dodecylphenylsulfonyl)oxy]-1,3-diphenyl-1-ethanone and 2-[(4-tolylsulfonyl)oxy]-propionic acid, is hardened by heat.

An additionally preferred process is one in which an acid-hardenable composition containing at least one hardening catalyst of the formula I with n=1, in which $R^1$ is $C_1$–$C_{12}$-alkyl which is unsubstituted or substituted by —OR, —Cl or phenyl, where R is hydrogen, $C_1$–$C_4$-alkyl or —SO$_2$—$R^4$, where $R^4$ is as defined below, or in which $R^1$ is —OH, $R^2$ is hydrogen and $R^3$ is hydrogen, $C_1$–$C_8$-alkyl which is unsubstituted or substituted by —OR, —COOH or phenyl, where R is hydrogen, $C_1$–$C_4$-alkyl or —SO$_2$—$R_4$ where $R^4$ is as defined below, or in which $R^3$ is phenyl which is unsubstituted or substituted by —Cl, —Br, $C_1$–$C_4$-alkoxy or $C_1$–$C_{12}$-alkyl, and $R^4$ is $C_1$–$C_{18}$-alkyl, phenyl which is unsubstituted or substituted by $C_1$–$C_{15}$-alkyl, or naphthyl which is unsubstituted or substituted by $C_1$–$C_{18}$-alkyl, is hardened by heat.

An additionally particularly preferred process is one in which an acid-hardenable composition containing at least one hardening catalyst of the formula I with n=1, in which $R^1$ is $C_1$–$C_8$-alkyl which is unsubstituted or substituted by —OR, where R is hydrogen, $C_1$–$C_4$-alkyl or —SO$_2$—$R^4$, where $R^4$ is as defined below, or in which $R^1$ is —OH, $R^2$ is hydrogen and $R^3$ is hydrogen, $C_1$–$C_8$-alkyl which is unsubstituted or substituted by —OR or —COOH, where R is hydrogen, $C_1$–$C_4$-alkyl or —SO$_2$—$R^4$, where $R^4$ is as defined below, or in which $R^3$ is phenyl which is unsubstituted or substituted by —Cl or $C_1$–$C_{12}$-alkyl, and $R^4$ is $C_1$–$C_{18}$-alkyl, phenyl which is unsubstituted or substituted by $C_1$–$C_{15}$-alkyl or naphthyl which is unsubstituted or substituted by $C_1$–$C_{18}$-alkyl, is hardened by heat.

The invention furthermore relates to an acid-hardenable composition containing at least one hardening catalyst of the formula I with n=1, in which $R^1$ is —OH, $R^2$ is hydrogen, $R^3$ is $C_1$–$C_8$-alkyl and $R^4$ is methyl, phenyl, tolyl or dodecylphenyl, and, preferably, $R^1$ is —OH, $R^2$ is hydrogen, $R^3$ is $C_1$–$C_4$-alkyl and $R^4$ is phenyl or tolyl, and, particularly preferably, the hardening catalyst is 2-[(4-tolylsulfonyl)oxy]-propionic acid.

Many compounds of the formula I are known and can be prepared by known processes, for example by reacting the corresponding hydroxy compounds of the formula III

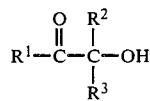   (III)

with one or half an equivalent of the corresponding mono- or di-sulfonic acid chlorides of the formula IV $R^4(SO_2Cl)_n$   (IV)

in the presence of a base (in this context, cf.: "Journal of the Chemical Society Perkin I, 1981, page 263" or "Journal of Organic Chemistry 34, 1595 (1969)"), or by reacting the corresponding bromine derivatives of the formula V

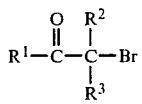   (V)

with one or half an equivalent of the silver salts of the corresponding mono- or di-sulfonic acid derivatives of the formula VI $(AgO_3S)_nR^4$   (VI)

such as, for example, by the process described in "Journal of Organic Chemistry of the USSR, volume 8, page 2166 (1972)", or, for a particular class of this compound, by direct reaction of an acetophenone of the formula VII with the iodonium salt of the formula VIII to give the corresponding product of the formula IX

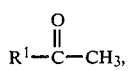   VII

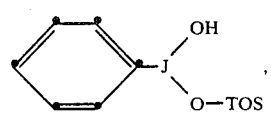   VIII

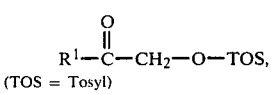   IX (TOS = Tosyl)

for example by the process described in "Journal of Organic Chemistry 47, 2487 (1982)".

In formulae III, IV, V, VI, VII and IX, the radicals $R^1$ to $R^4$ and n are as defined above.

Many intermediates of the formulae III, IV, V, VI and VII are known compounds which can be prepared by known processes, for example by those described in "Houben-Weyl, Methoden der organischen Chemie (Methods of organic chemistry)", volume V/4, pages 171–189, for compounds of the formula V, volume IX, pages 411 and 563, for compounds of the formula IV, and the literature references "A. 526, 143, 164 (1936), Am. Soc. 76, 4402 (1954) or Z.Obsc. Chim. 34, 3165 (1964)", for compounds of the formula III.

Suitable acid-hardenable resins are all resins of which the hardening can be accelerated by acid catalysts. These are, in particular, varnishes based on acrylic, polyester, alkyd, melamine, urea and phenolic resins, but especially mixtures of acrylic, polyester or alkyd resins with one another or with a melamine resin. This also includes modified varnish gums, for example acrylic-modified polyester or alkyd resins. Examples of individual types of resins which fall within the expression acrylic, polyester and alkyd resins are described, for example, in "Wagner/Sarx: Lackkunstharze (synthetic varnish gum), Munich 1971, pages 86–123 and pages 229–238" or in "Ullmann, Encyclopädie der technischen Chemie (Encyclopedia of industrial chemistry), 4th edition, volume 15 (1978), pages 613–628", European Patent No. 44,115, U.S. Pat. No. 4,307,208, U.S. Pat. No. 4,371,605 and German Offenlegungsschrift No. 2,842,002. Acid catalysis is of particular importance for the hardening of varnishes containing etherified amino resins, for example methylated or butylated melamine resins (N-methoxymethyl- or N-butoxymethyl-melamine or methylated/butylated glycol urils and the like) for example

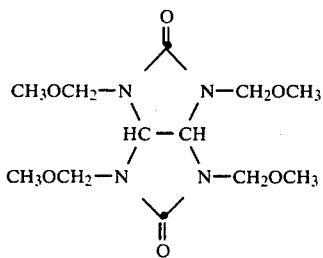

Other resin compositions are mixtures of aryl and polyester resins containing polyfunctional alcohols or hydroxyl groups, partially hydrolysed polyvinyl acetate and polyvinyl alcohol with polyfunctional dihydropyranyl ethers, for example derivatives of 3,4-dihydro-2H-pyran-2-carboxylic acid.

Resin compositions which have monomeric or oligomeric constituents with unsaturated groups which are capable of undergoing polymerisation are used for particular purposes. Such resin compositions can also be hardened by the process according to the invention. In this case, free radical polymerisation initiators can additionally also be used; these initiate polymerisation of the unsaturated groups during the heat treatment.

The varnishes can be solutions or dispersions of the varnish gum in an organic solvent or in water, but they can also be solvent-free. Varnishes with a low solvent content, so-called "high solid" varnishes are of particular interest. The varnishes can be clear varnishes, such as are used, for example, in the automobile industry as a covering varnish for multi-layer paints. They can also contain pigments, either inorganic or organic pigments, and a metal powder for metallic effect varnishes.

Examples of polymerisable compounds with one or more polymerisable, ethylenically unsaturated bonds are esters of acrylic and methacrylic acid, hydroxyethyl esters of acrylic and methacrylic acid, di- and poly-acrylates and di- and poly-methacrylates of glycols and polyols, aromatic vinyl and divinyl derivatives, N-methylol derivatives of acrylamide or methacrylamide, vinyl alkyl ethers, trimethylolpropanediallyl ether mono-(meth)-acrylates, reaction products of glycidyl(meth)acrylate and mono- or di-carboxylic acids, polyester resins of $\alpha,\beta$-unsaturated dicarboxylic acids or anhydrides thereof and diols, urethane acrylates or polyepoxy polyacrylates.

The varnishes can furthermore contain relatively small amounts of particular additives such as are customary in varnish technology, for example flow control agents, thixotropic agents, light stabilisers or antioxidants.

Examples of light stabilisers are those of the class of hydroxyphenyl-benzotriazoles, hydroxybenzophenones, cyanoacrylates, hydroxyphenyl-triazines, oxalanilides, organic nickel compounds and polyalkyl-piperidine derivatives.

Polymethylpiperidine derivatives and combinations thereof with UV absorbers are preferably used.

The hardening catalysts of the formulae I and II are added to the resins in an amount sufficient for hardening. The amount required depends not only on the nature of the resin but also on the intended hardening temperature and hardening time. The hardening times are generally between 0.1 and 60 minutes, preferably between 1 and 30 minutes, and the hardening temperatures are generally in a range from 110° to 300° C., but preferably within 120° to 250° C. and in particular 120° to 150° C. Moreover, 0.1 to 10% by weight of hardening catalyst, preferably 1-5% by weight of hardening catalyst, is used, based on the solvent-free resin. Mixtures of the hardening catalysts can also be reacted.

The present process according to the invention can be applied to all types of industrial surface coating and varnishing. This includes, inter alia, varnishing of vehicles, ships, machines and structural components. The importance of the process according to the invention in varnishing of automobiles, both for single-layer and for multilayer varnishing, is to be particularly emphasised. It is particularly important that this process can be used with the so-called "high solid" industrial varnishes which require only small amounts of solvent—if any—which will become increasingly of interest in the future in view of protection of the environment and work safety (waste air, effluent, safety equipment). The process can also be applied to continuous coating of sheet metal, for example sheet steel or aluminium, by the coil coating process. The process can also be used for hardening acid-hardenable printing inks, since these are particularly suitable for can varnishing because of their excellent absorbancy. This process can also be used for wooden components, which can be given either a colourless or a pigmented coating.

In addition to the possible uses already mentioned, the process according to the invention can be used on pressing compositions and casting and laminating resins, the resins being activated by heat in the presence of the latent hardening catalysts, with simultaneous shaping and hardening.

The examples below illustrate in more detail the preparation of some compounds used in the process according to the invention.

EXAMPLE 1

Preparation of 2-[4-(tolylsulfonyl)oxy]-3-pentanone 19.6 g (0.05 mol) of the iodonium salt of the formula VIII are dissolved in 125 ml of acetonitrile in a flask and the solution is warmed to the reflux temperature (about 80° C.). 50 ml (0.047 mol) of pentan-3-one are rapidly added at this temperature and the mixture is subsequently stirred under reflux for a further 15 minutes. The reaction solution is then concentrated, the residue is dissolved in methylene chloride and the solution is washed with water. The organic phase is dried, and concentrated again. A clear light brown oil remains, which crystallises out in hexane in the cold to give a white crystalline powder with a melting point of 45° C. to 46° C. in a yield of 6.7 g, corresponding to 55.6% of theory.

Analysis: Calculated: C 56.03%, H 6.29%, O 24.97%, S 12.51%, Found: C 56.47%, H 6.30%, O 25.09%, S 12.48%.

EXAMPLE 2

Preparation of 2-[(4-tolylsulfonyl)oxy]propionic acid morpholide 7.5 g (30 mmol) of 2-[(4-tolylsulfonyl)oxy]-propionyl chloride are dissolved in 15 ml of tetrahydrofuran in a flask. 6.5 g (80 mmol) of morpholine are then slowly added dropwise at 0°-5° C., with stirring and simultaneous cooling. The mixture is then subsequently stirred at 0° C., poured onto ice and extracted with diethyl ether. The organic phase is separated off, dried with Na₂SO₄ and concentrated in a rotary vacuum evaporator. The light yellow residue is separated on a silica gel column (eluting agent: hexane/ethyl acetate 1:1). White crystals of melting point 75°–77° C. then result.

Elemental analysis: calculated: C 53.66%, H 6.11%, N 4.47%, S 10.23%, found: C 53.57%, H 6.11%, N 4.43%, S 10.29%.

EXAMPLE 3

Preparation of 2-[(4-tolylsulfonyl)oxy]butanal 7.2 g (35 mmol) of 2-bromobutanal (prepared from butanal and CuBr₂ in isopropanol/water 72:25) and 12.0 g (42 mmol) of silver tosylate are stirred in 100 ml of acetonitrile in a flask at 40° C. After 12 hours the light green suspension is filtered and the filtrate is concentrated. The residue is taken up in 50 ml of methylene chloride and is filtered again and concentrated. The oil is separated on a silica gel column (eluting agent: hexane/ethyl acetate 1:1). An oil results.

The following example illustrates the process according to the invention in more detail, in which an acid-hardenable composition containing a latent hardening catalyst of the formula I or II is hardened by heat, with the aid of a specific composition. In this example, parts and percentages are by weight.

EXAMPLE 4

Hardening of a varnish based on acrylic/melamine resin

A high solid clear varnish having the following composition is applied to aluminium sheets 0.5 mm thick which are coated with a silver metallic varnish, as the priming varnish, based on cellulose acetobutyrate or polyester/melamine resin:

|  |  | Solids |
|---|---|---|
| Hexamethoxymethylmelamine (Cymel ® 301, 100%) | 17.93 g | 17.93 parts |
| Butyl acetate | 9.73 g |  |
| Cellulose acetobutyrate (CAB ® 551001 from Eastman Chem.) | 1.83 g |  |
| Silicon resin in organic solvent (flow control agent Byketol ® Spezial from Byk-Mallinckrodt) | 2.80 g |  |
| Flow control agent on a polymer basis (Medaflow ®, 1% solution; Monsanto) | 0.29 g |  |
| Acrylic resin containing hydroxyl groups (Paraloid ® AT 410, 73% by weight; Rohm + Haas) | 57.30 g | 41.83 parts |
| n-butanol | 10.12 g |  |
|  | 100.00 g | 59.76 parts |

The catalysts are predissolved in a mixture of methyl amyl ketone/butyl glycol acetate in a ratio of 30:70 and are added to the varnish.

The compounds shown in Table 1 are incorporated into this resin formulation in a concentration of 1 or 2% by weight (based on the solvent-free binder = 59.76 parts).

The varnish is applied with an electrical film-drawing apparatus such that the dry film thickness is about 45 μm. After an airing time of 15 minutes, the varnish is then stoved at 120° C. and 130° C.

To evaluate the degree of hardness, the pendulum hardness of the film of varnish is determined by the König method (DIN 53 157) after storage for 3 days.

To evaluate the discolouration (yellowing), the colour shade interval ΔE is determined according to DIN 6174 also after 3 days.

The storage stability of the varnish samples is also determined by measuring the viscosity with an ICI ball-plate viscometer (DIN 53 229). A 50 ml glass is filled with catalysed clear varnish solution (cf. recipe without spray diluter) and the initial viscosity of the solution is determined using an ICI ball-plate viscometer. The samples are then stored in an oven at 40° C. or 60° C. and the viscosity is measured every 24 hours, the number of days the samples take to gel being determined.

The results can be seen from the following Table 1.

TABLE 1

| Catalyst Formula | Percent % | Stoving time 30 minutes Stoving temperature 120° C. | | Stoving time 30 minutes Stoving temperature 130° C. | | Storage stability | |
|---|---|---|---|---|---|---|---|
|  |  | Pendulum hardness (s) | Colour shade separation ΔE | Pendulum hardness (s) | Colour shade separation ΔE | at 40° C. (Days to gelling) | at 60° C. (Days to gelling) |
| 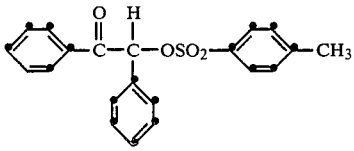 4a | 2 | 134 | 1.1 | 190 | 1.0 | 17 | — |
| 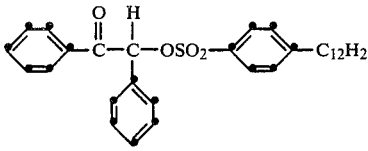 4b | 2 | 119 | 1.2 | 183 | 1.3 | 20 | — |

TABLE 1-continued

| Catalyst | | Stoving time 30 minutes Stoving temperature 120° C. | | Stoving time 30 minutes Stoving temperature 130° C. | | Storage stability | |
|---|---|---|---|---|---|---|---|
| Formula | Percent % | Pendulum hardness (s) | Colour shade separation ΔE | Pendulum hardness (s) | Colour shade separation ΔE | at 40° C. (Days to gelling) | at 60° C. (Days to gelling) |
| 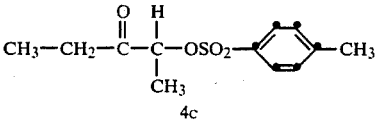 CH₃—CH₂—C(=O)—C(H)(CH₃)—OSO₂—C₆H₄—CH₃  4c | 1 | 165 | 4 | 183 | 4 | — | 7 |

The results shown in Table 2 have been obtained by methods analogous to those already described. Changes have been made in the determination of the degree of hardness; in this case, the pendulum hardness is measured after 24 hours. Furthermore, the storage stability is determined differently, in particular the increase in viscosity of the samples after 7 days is given in per cent in comparison with the initial viscosity.

TABLE 2

| Catalyst | Percent % | Stoving time 30 minutes Stoving temperature 120° C. | | Stoving time 30 minutes Stoving temperature 130° C. | | Storage stability (increase in viscosity after 7 days of storage at 40° C.; in % compared with the initial viscosity) |
|---|---|---|---|---|---|---|
| | | Pendulum hardness (s) | Colour shade separation ΔE | Pendulum hardness (s) | Colour shade separation ΔE | |
| no catalyst added | | 18 | 0.3 | 23 | 0.4 | |
| p-toluene sulfonic acid | 1 | 189 | 0 | 203 | 0 | gelled after only one day |
| 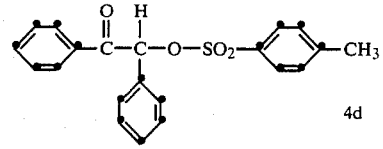 4d | 1 2 | 165 178 | 0.3 0.1 | 183 180 | 0.1 0.1 | 53 107 |
| 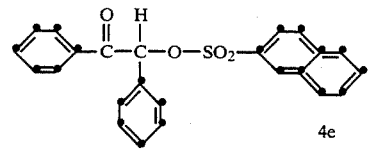 4e | 1 2 | 166 192 | 0 0 | 176 196 | 0.3 0.2 | 74 147 |
| 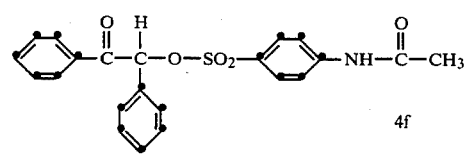 4f | 1 2 | 178 186 | 0.2 0 | 192 204 | 0.1 0.1 | 44 — |
| 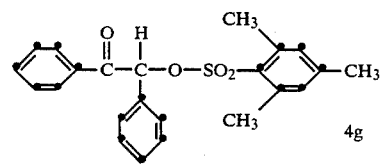 4g | 1 2 | 85 133 | 0.1 0.2 | 179 192 | 0.2 0.1 | 28 61 |
| 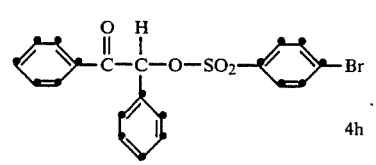 4h | 1 2 | 193 201 | 0.1 0.1 | 195 202 | 0.1 0 | 179 333 |

TABLE 2-continued

| Catalyst | Percent % | Stoving time 30 minutes Stoving temperature 120° C. | | Stoving time 30 minutes Stoving temperature 130° C. | | Storage stability (increase in viscosity after 7 days of storage at 40° C.; in % compared with the initial viscosity) |
| --- | --- | --- | --- | --- | --- | --- |
| | | Pendulum hardness (s) | Colour shade separation ΔE | Pendulum hardness (s) | Colour shade separation ΔE | |
| 4i | 1 | 114 | 0.3 | 190 | 0.1 | 47 |
| | 2 | 161 | 0.3 | 190 | 0.3 | 71 |
| 4j | 1 | 182 | 0.4 | 200 | 0.3 | 70 |
| | 2 | 183 | 0.6 | 194 | 0.5 | 106 |
| 4k | 1 | 195 | 0.2 | 201 | 0 | 135 |
| 4l | 1 | 202 | 0.1 | 204 | 0.3 | 110 |
| 4m | 1 | 96 | 0.3 | 200 | 0.4 | 36 |
| 4n | 1 | 20 | 0.4 | 128 | 0.4 | 14 |
| | 2 | — | — | 168 | 0.5 | — |

What is claimed is:

1. A process for the hardening of an acid-hardenable composition which comprises an acid-hardenable resin; and 0.1 to 10% by weight of at least one latent hardening catalyst of formula I or II

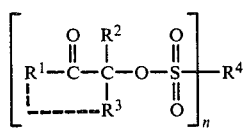
(I)

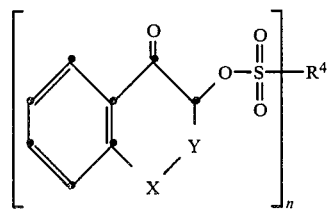
(II)

in which, in both formulae, n is 1 or 2, $R^1$ is phenyl which is unsubstituted or mono-, di- or tri-substituted by —Cl, —Br, $C_1$-$C_{12}$-alkyl, $C_1$-$C_4$-alkoxy, phenyl or phenoxy, naphthyl which is unsubstituted or mono-, di- or tri-substituted by —Cl, —Br or $C_1$-$C_{12}$-alkyl, $C_1$-$C_{12}$-alkyl which is unsubstituted or mono- or poly-substituted by —OR, —Cl, —Br, phenyl or cyloalkyl, where R is hydrogen, $C_1-C_4$-alkyl or $-SO_2-R^4$, where $R^4$ is as defined below, or in which $R^1$ is $C_1-C_{12}$-alkenyl which is unsubstituted or substituted by phenyl, or hydrogen, —OH, $C_5-C_7$-cycloalkoxy or $C_5-C_7$-cycloalkyl or $-NH_2$, $-NHR^5$, $-N(R^5)_2$ or $-N-H-CO-R^5$, where $R^5$ is $C_1-C_4$-alkyl or phenyl, or in which $R^1$ is morpholinyl, piperidinyl, pyridyl, furyl, thienyl, tetrahydrofuranyl, tetrahydronaphthyl or indolyl, $R^2$ is hydrogen, $R^3$ is hydrogen, $C_1-C_8$-alkyl which is unsubstituted or mono-or poly-substituted by —OR, —Cl, —CN, —COOH, phenyl, chlorophenyl, $C_7-C_{10}$-alkylphenyl or $C_7-C_{10}$-alkoxy-phenyl, where R is hydrogen, $C_1-C_4$-alkyl or $-SO_2-R^4$, where $R^4$ is as defined below, or in which $R^3$ is phenyl which is unsubstituted or mono-or poly-substituted by —Cl, —Br, $C_1-C_{12}$-alkyl, $C_1-C_4$-alkoxy, phenyl or phenoxy, or —CH, —COOH, benzoyl, $-CONH_2$, $-CONHR^5$, $CON(R^5)_2$,

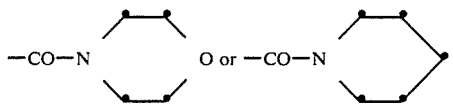

where $R^5$ is $C_1-C_4$-alkyl or phenyl, or $R^1$ and $R^3$, together with the carbon atoms to which they are bonded, form a $C_5-C_7$-cycloalkyl ring, X is —O—, —S—, $-SO_2-$, $-CH_2-$, $-C(CH_3)_2-$ or $>N-COR^5$, where $R^5$ is $C_1-C_4$-alkyl or phenyl, Y is a direct bond or $-CH_2-$ and, if n=1, $R^4$ is $C_1-C_{18}$-alkyl, phenyl which is unsubstituted or mono-, di- or tri-substituted by halogen, $C_1-C_{18}$-alkyl, $C_1-C_4$-alkoxy, —CONH— ($C_1-C_4$-alkyl), $-CONH-C_6H_5$, $-NO_2$ or benzoyl, naphthyl which is unsubstituted or mono-, di- or tri-substituted by halogen, $C_1-C_{12}$-alkyl or $C_1-C_4$-alkoxy, and $R^4$ is moreover $C_5-C_6$-cycloalkyl, $C_7-C_9$-aralkyl, camphoryl, $-CF_3$, $-CCl_3$ or $-NH_2$, and, if n=2, $R^4$ is a $-(CH_2)_m$-group, where m is a number from 2 to 8, or is phenylene or naphthylene, each of which is unsubstituted or mono- or poly-substituted by $C_1-C_{12}$-alkyl, which process comprises heating the composition at a temperature of 120° to 250° C.

2. A process according to claim 1, wherein, in the hardening catalysts of the formula I, n=1 and $R^1$ is phenyl which is unsubstituted or substituted by —Cl, —Br or $C_1-C_{12}$-alkyl, naphthyl which is unsubstituted or substituted by —Cl, —Br or $C_1-C_{12}$-alkyl, or $C_1-C_{12}$-alkyl which is unsubstituted or substituted by —OR, —Cl or phenyl, where R is hydrogen, $C_1-C_4$-alkyl or $-SO_2-R^4$, where $R^4$ is as defined below, or in which $R^1$ is hydrogen or —OH, $R^2$ is hydrogen and $R^3$ hydrogen, $C_1-C_8$-alkyl which is unsubstituted or substituted by —OR, —Cl, —COOH or phenyl, where R is hydrogen, $C_1-C_4$-alkyl or $-SO_2-R^4$, where $R^4$ is as defined below, or in which $R^3$ is phenyl which is unsubstituted or substituted by —Cl, —Br, $C_1-C_4$-alkoxy or $C_1-C_{12}$-alkyl, $R_4$ is $C_1-C_{18}$-alkyl, camphoryl, phenyl which is unsubstituted or substituted by —Cl, —Br, $C_1-C_{18}$-alkyl or acetamido, or naphthyl which is unsubstituted or substituted by —Cl, —Br or $C_1-C_{18}$-alkyl.

3. A process according to claim 1, wherein, in the hardening catalysts of the formula I, n is 1 and $R^1$ is phenyl which is unsubstituted or substituted by —Cl, —Br or $C_1-C_4$-alkyl, $C_1-C_{12}$-alkyl which is unsubstituted or substituted by —OR, —Cl or phenyl, where R is hydrogen, $C_1-C_4$-alkyl or $-SO_2-R^4$, where $R^4$ is as defined below, or in which $R^1$ is —OH, $R^2$ is hydrogen and $R^3$ is $C_1-C_8$-alkyl which is unsubstituted or substituted by —OR, —COOH, or phenyl, where R is hydrogen, $C_1-C_4$-alkyl or $-SO_2-R^4$, where $R^4$ is as defined below, or in which $R^3$ is phenyl which is unsubstituted or substituted by —Cl, —Br, $C_1-C_4$-alkoxy or $C_1-C_{12}$-alkyl, and $R^4$ is $C_1-C_{18}$-alkyl, phenyl which is unsubstituted or substituted by $C_1-C_{15}$-alkyl or naphthyl which is unsubstituted or substituted by $C_1-C_{18}$-alkyl.

4. A process according to claim 1, wherein, in the hardening catalysts of the formula I, n is 1 and $R^1$ is phenyl which is unsubstituted or substituted by —Cl or $C_1-C_4$-alkyl, $C_1-C_8$-alkyl which is unsubstituted or substituted by —OR, where R is hydrogen, $C_1-C_4$-alkyl or $-SO_2-R^4$, where $R^4$ is as defined below, or in which $R^1$ is —OH, $R^2$ is hydrogen and $R^3$ is hydrogen, $C_1-C_8$-alkyl which is unsubstituted or substituted by —OR or —COOH, where R is hydrogen, $C_1-C_4$-alkyl or $-SO_2-R^4$, where $R^4$ is as defined below, or in which $R^3$ is phenyl which is unsubstituted or substituted by —Cl or $C_1-C_{12}$-alkyl, and $R^4$ is $C_1-C_{18}$-alkyl, phenyl which is unsubstituted or substituted by $C_1-C_{15}$-alkyl or naphthyl which is unsubstituted or substituted by $C_1-C_{18}$-alkyl.

5. A process according to claim 1, wherein, in the hardening catalysts of the formula I, n is 1 and $R^1$ is phenyl which is unsubstituted or substituted by —Cl or methyl, or is —OH, $R^2$ is hydrogen and $R^3$ is hydrogen, $C_1-C_8$-alkyl which is unsubstituted or substituted by —OR, where R is hydrogen, $C_1-C_4$-alkyl or $-SO_2-R^4$, where $R^4$ is as defined below, or in which $R^3$ is phenyl which is unsubstituted or substituted by methyl, and $R^4$ is methyl, or phenyl which is unsubstituted or substituted by $C_9-C_{15}$-alkyl or methyl.

6. A process according to claim 1, wherein the compound of the formula I with n=1 used as the latent hardening catalyst is chosen from the group consisting of 2-[(4-tolylsulfonyl)oxy]-1,2-diphenyl-1-ethanone, 2-[(4-dodecylphenylsulfonyl)oxy]-1,2-diphenyl-1-ethanone and 2-[(4-tolylsulfonyl)oxy]-propionic acid.

7. A process according to claim 1, wherein, in the hardening catalysts of the formula I, n is 1 and $R^1$ is $C_1-C_{12}$-alkyl which is unsubstituted or substituted by —OR, —Cl or phenyl, where R is hydrogen, $C_1-C_4$-alkyl or $-SO_2-R^4$, where $R^4$ is as defined below, or in which $R^1$ is —OH, $R^2$ is hydrogen and $R^3$ is hydrogen, $C_1-C_8$-alkyl which is unsubstituted or substituted by —OR, —COOH, or phenyl, where R is hydrogen, $C_1-C_4$-alkyl or $-SO_2-R^4$, where $R^4$ is as defined below, or in which $R^3$ is phenyl which is unsubstituted or substituted by —Cl, —Br, $C_1-C_4$-alkoxy or $C_1-C_{12}$-alkyl, and $R^4$ is $C_1-C_{18}$-alkyl, phenyl which is unsubstituted or substituted by $C_1-C_{15}$-alkyl, or naphthyl which is unsubstituted or substituted by $C_1-C_{18}$-alkyl.

8. A process according to claim 1, wherein, in the hardening catalysts of the formula I, n is 1 and $R^1$ is $C_1-C_8$-alkyl which is unsubstituted or substituted by —OR, where R is hydrogen, $C_1-C_4$-alkyl or $-SO_2-R^4$, where $R^4$ is as defined below, or in which $R^1$ is —OH, $R^2$ is hydrogen and $R^3$ is hydrogen, $C_1-C_8$-alkyl which is unsubstituted or substituted by —OR or —COOH, where R is hydrogen, $C_1-C_4$alkyl or $-SO_2-R^4$, where $R^4$ is as defined below, or in which $R^3$ is phenyl which is unsubstituted or substituted by —Cl or $C_1-C_{12}$-alkyl, and $R^4$ is $C_1-C_{18}$-alkyl, phenyl which is unsubstituted or substituted by $C_1-C_{15}$-alkyl or naphthyl which is unsubstituted or substituted by $C_1-C_{18}$-alkyl.

9. A process according to claim 1 wherein the acid-hardenable resin is an acrylic resin, a polyester, an alkyd resin, a melamine resin, a urea resin, a phenolic resin or mixtures thereof.

10. A heat-curable, acid-hardenable composition which comprises
(a) an acid-hardenable resin, and
(b) 0.1 to 10% by weight of a least one latent hardening catalyst of formula I

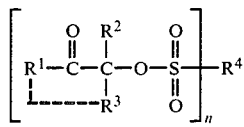

in which n is 1 or 2, $R^1$ is $C_1$–$C_{12}$-alkyl which is unsubstituted or mono- or poly-substituted by —OR, —Cl, —Br, phenyl or cyloalkyl, where R is hydrogen, $C_1$–$C_4$-alkyl or —$SO_2$—$R^4$ where $R^4$ is as defined below, or in which $R^1$ is $C_1$–$C_{12}$-alkenyl which is unsubstituted or substituted by phenyl, or $R^1$ is hydrogen, —OH, $C_5$–$C_7$-cycloalkoxy or $C_5$–$C_7$-cyloalkyl or —$NH_2$, —$NHR^5$, —$N(R^5)_2$ or —NH—CO—$R^5$, where $R^5$ is $C_1$–$C_4$-alkyl or phenyl, or in which $R^1$ is morpholinyl or piperidinyl, $R^2$ is hydrogen, $R^3$ is hydrogen, $C_1$–$C_9$-alkyl which is unsubstituted or mono- or poly-substituted by —OR, —Cl, —CN, —COOH, phenyl, chlorophenyl, $C_7$–$C_{10}$-alkylphenyl or $C_7$–$C_{10}$-alkoxy-phenyl, where R is hydrogen, $C_1$–$C_4$-alkyl or —$SO_2$—$R^4$. where $R^4$ is as defined below, or in which $R^3$ is phenyl which is unsubstituted or mono- or poly-substituted by —Cl, —Br, $C_1$–$C_{12}$-alkyl, $C_1$–$C_4$-alkoxy, phenyl or phenoxy, or —CN, —COOH, benzoyl, —$CONH_2$, —$CONHR^5$, $CON(R^5)_2$,

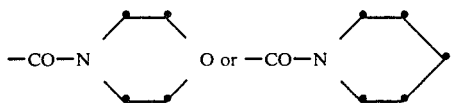

where $R^5$ is $C_1$–$C_4$-alkyl or phenyl, and if n=1, $R^4$ is $C_1$–$C_{18}$-alkyl, phenyl which is unsubstituted or mono-, di- or tri-substituted by halogen, $C_1$–$C_{18}$-alkyl, $C_1$–$C_4$-alkoxy, —CONH— ($C_1$–$C_4$-alkyl), —CONH—$C_6H_5$, —$NO_2$ or benzoyl, naphthyl which is unsubstituted or mono-, di- or tri-substituted by halogen, $C_1$–$C_{12}$-alkyl or $C_1$–$C_4$-alkoxy, and $R^4$ is moreover $C_5$–$C_6$-cycloalkyl, $C_7$–$C_9$-aralkyl, camphoryl, —$CF_3$, —$CCl_3$ or —$NH_2$, and, if n=2, $R^4$ is a —$(CH_2)_m$-group, where m is a number from 2 to 8, or is phenylene or naphthylene, each of which is unsubstituted or mono- or poly-substituted by $C_1$–$C_{12}$-alkyl.

11. A composition according to claim 9 which contains at least one hardening catalyst of the formula I with n=1, in which $R^1$ is —OH, $R^2$ is hydrogen, $R^3$ is $C_1$–$C_8$-alkyl and $R^4$ is methyl, phenyl, tolyl or dodecylphenyl.

12. A composition according to claim 10, containing at least one hardening catalyst in which $R^1$ is —OH, $R^2$ is hydrogen, $R^3$ is $C_1$–$C_4$-alkyl and $R^4$ is phenyl or tolyl.

13. A composition according to claim 10, containing at least the hardening catalyst 2-[(4tolylsulfonyl)oxy]-propionic acid.

14. A composition according to claim 10 wherein the acid-hardenable resin is an acrylic resin, a polyester, an alkyd resin, a melamine resin, a urea resin, a phenolic resin or mixtures thereof.

* * * * *